(12) United States Patent
Piccionelli et al.

(10) Patent No.: US 8,372,093 B2
(45) Date of Patent: Feb. 12, 2013

(54) SYSTEMS AND PROCESSES FOR CONTROLLING GASTRIC BANDS BASED ON GEOGRAPHIC LOCATION

(75) Inventors: Gregory Piccionelli, Westlake Village, CA (US); Ted Rittmaster, Westlake Village, CA (US)

(73) Assignee: Koletry Processing L.L.C., Dover, DE (US)

( * ) Notice: Subject to any disclaimer, the term of this patent is extended or adjusted under 35 U.S.C. 154(b) by 565 days.

(21) Appl. No.: 12/589,794

(22) Filed: Oct. 27, 2009

(65) Prior Publication Data

US 2010/0114132 A1    May 6, 2010

Related U.S. Application Data

(60) Provisional application No. 61/198,285, filed on Nov. 4, 2008.

(51) Int. Cl.
*A61B 5/103* (2006.01)
*A61B 17/00* (2006.01)
*A61F 2/00* (2006.01)
*G08B 23/00* (2006.01)

(52) U.S. Cl. .......................... 606/151; 600/37

(58) Field of Classification Search .............. 600/32, 600/37, 593; 128/899; 607/30, 32, 60; 623/14.13, 623/23.65; 606/157, 507

See application file for complete search history.

(56) References Cited

U.S. PATENT DOCUMENTS

| 4,592,339 | A | * | 6/1986 | Kuzmak et al. | 606/157 |
|---|---|---|---|---|---|
| 5,226,429 | A | * | 7/1993 | Kuzmak | 606/157 |
| 5,396,227 | A | * | 3/1995 | Carroll et al. | 340/573.4 |
| 5,449,368 | A | * | 9/1995 | Kuzmak | 606/157 |
| 5,731,757 | A | * | 3/1998 | Layson, Jr. | 340/573.1 |
| 5,752,976 | A | * | 5/1998 | Duffin et al. | 607/32 |
| 5,782,778 | A | * | 7/1998 | De Briere et al. | 600/587 |
| 5,938,669 | A | * | 8/1999 | Klaiber et al. | 606/157 |
| 5,982,281 | A | * | 11/1999 | Layson, Jr. | 340/539.13 |
| 6,043,748 | A | * | 3/2000 | Touchton et al. | 340/573.3 |
| 6,067,991 | A | * | 5/2000 | Forsell | 128/899 |
| 6,102,922 | A | * | 8/2000 | Jakobsson et al. | 606/157 |
| 6,160,481 | A | * | 12/2000 | Taylor, Jr. | 340/573.4 |
| 6,210,347 | B1 | * | 4/2001 | Forsell | 600/593 |
| 6,285,897 | B1 | * | 9/2001 | Kilcoyne et al. | 600/350 |
| 6,450,946 | B1 | * | 9/2002 | Forsell | 600/37 |
| 6,454,699 | B1 | * | 9/2002 | Forsell | 600/30 |
| 6,461,292 | B1 | * | 10/2002 | Forsell | 600/31 |
| 6,461,293 | B1 | * | 10/2002 | Forsell | 600/37 |
| 6,470,892 | B1 | * | 10/2002 | Forsell | 128/899 |
| 6,556,819 | B2 | * | 4/2003 | Irvin | 455/410 |
| 6,659,936 | B1 | * | 12/2003 | Furness et al. | 600/30 |
| 7,338,433 | B2 | * | 3/2008 | Coe | 600/31 |
| 7,351,240 | B2 | * | 4/2008 | Hassler et al. | 604/891.1 |
| 7,434,541 | B2 | * | 10/2008 | Kates | 119/720 |
| 7,442,165 | B2 | * | 10/2008 | Forsell | 600/38 |
| 7,621,863 | B2 |  | 11/2009 | Forsell |  |
| 2003/0019498 | A1 | * | 1/2003 | Forsell | 128/898 |
| 2003/0066536 | A1 | * | 4/2003 | Forsell | 128/899 |

(Continued)

*Primary Examiner* — Carl H Layno
*Assistant Examiner* — Erin Piateski

(57) ABSTRACT

A system and process employs a gastric band device having an adjustable restriction amount that is adjustable based on at least one first control signal. The system and process also employs at least one of a wireless receiver and location detection electronics configured for providing at least one second signal. In addition, a controller is configured to provide at least one first control signal to the gastric band device based at least in part on at least one second control signal from at least one of the wireless receiver and the location detection electronics. The controller may be configured to provide at least one first control signal for one of increasing restriction or reducing restriction of the gastric band in response to receiving a signal from the location detection electronics representing a predefined geographic location.

31 Claims, 3 Drawing Sheets

U.S. PATENT DOCUMENTS

| | | | |
|---|---|---|---|
| 2003/0172940 A1* | 9/2003 | Rogers et al. | 128/899 |
| 2006/0173238 A1* | 8/2006 | Starkebaum | 600/37 |
| 2007/0173705 A1* | 7/2007 | Teller et al. | 600/300 |
| 2008/0097188 A1* | 4/2008 | Pool et al. | 600/409 |
| 2008/0172072 A1* | 7/2008 | Pool et al. | 606/151 |
| 2008/0250341 A1* | 10/2008 | Dlugos et al. | 715/771 |
| 2009/0192534 A1* | 7/2009 | Ortiz et al. | 606/157 |
| 2009/0209985 A1* | 8/2009 | Khalili | 606/157 |

* cited by examiner

SYSTEMS AND PROCESSES FOR CONTROLLING GASTRIC BANDS BASED ON GEOGRAPHIC LOCATION

RELATED APPLICATIONS

The present application relates to U.S. Provisional Patent Application No. 61/198,285, filed Nov. 4, 2008, titled "Systems And Processes For Controlling Inflatable Members And Gastric Bands Based On Geographic Location," which is incorporated herein by reference in its entirety and from which priority is claimed.

BACKGROUND OF THE DISCLOSURE

1. Field of the Invention

Embodiments of the present invention relate to systems and processes for controlling inflatable members, such as, but not limited to, gastric bands, where the control is based, at least in part, on geographic location and/or signals communicated by wireless electronic communication. Other embodiments relate to systems and processes for controlling other types of bands or other inflatable members for medical, dietary, cosmetic or other treatments.

2. Related Art

A weight loss procedure, approved in the U.S. by the FDA in June 2001, called the Laparoscopic Adjustable Gastric Banding Procedure involves placing a band around the upper portion of a patient's stomach. Examples of such bands have become known as Lap-Bands. Such Adjustable Gastric Bands, including Lap-Bands, have been made of a hollow ring-shaped band of silicone or sylastic material. In typical Gastric Banding procedures, the band is placed around the upper portion (such as the upper third portion) of the stomach to create a small stomach pouch above the band. The small stomach pouch initially holds about 2 ounces of food, but eventually holds up to 4 to 6 ounces of food. The band allows food in the small stomach pouch to be slowly released into the lower portion of the stomach for digestion.

Nerves that signal the brain that the stomach is full are located in the upper area of the stomach. Accordingly, the restricted stomach space in the upper portion of the stomach causes a faster and longer lasting feeling of fullness.

A tube attached to the band has a port at one tube end. The port may be attached to abdominal muscles just below the patient's ribs. The port provides access to the interior of the band to allow the addition or removal of a fluid, such as saline, into the interior of the band, to control the band pressure by causing increased restriction of the stomach as the amount of fluid and/or fluid pressure increases or decreased restriction of the stomach as the amount of fluid and/or fluid pressure decreases.

The band may be surgically implanted, using laparoscopic surgical techniques or other suitable surgical techniques. After surgery, the band is empty. Typically, about six weeks after Lap-Band surgery, or whenever a plateau in weight loss is reached, a surgeon adds a small amount of saline in the band. Typically, the band can hold up to about 4 to 5 cc's of saline. However, for adjustments, only small amounts of saline need be added for each adjustment.

An adjustable gastric band device is described in U.S. Pat. No. 7,351,240, titled "Thermodynamically Driven Reversible Infuser Pump For Use As A Remotely Controlled Gastric Band."

With laparoscopic surgery, small incisions are made in the abdominal wall, then narrow and hollow tubes are inserted through the incisions to the surgical area. Instruments and cameras are passed through the tubes to perform the surgery. The camera allows the surgeon to see inside the abdomen. The surgeon positions the band around the stomach to form a ring and then fastens the lock which holds the band in place. During surgery, an access port may be placed beneath the skin. The access port is connected to the gastric band by a tube. Saline can be easily added or removed by the surgeon through the access port using a thin needle to inflate or deflate the band by specified amounts. For example, if weight loss is too gradual because the band is too loose, then saline may be added to reduce the opening between the upper and lower portions of the stomach. On the other hand, if the opening is too restricted, saline can be removed to enlarge the opening between the upper and lower portions of the stomach.

SUMMARY

Embodiments of the present invention relate to systems and processes for controlling a gastric band based, at least in part, on geographic location. The system includes, but is not limited to, a gastric band and adjustment mechanism that controls the size of the stoma, control electronics connected to control the adjustment mechanism and electronic memory associated with the control electronics. In addition, embodiments of the system also include one or both of transceiver electronics (such as, but not limited to receiver and/or transmitter electronics for wireless communication of signals) connected to the control electronics and location detection electronics connected to the control electronics. The transceiver electronics may be configured for communication with a remote communication and processing device. The location detection electronics provides a location signal corresponding to the geographic location of the system.

The control electronics are configured to control the operation of the adjustment mechanism to controllably adjust the gastric band, for example, in one or both of two adjustment directions (e.g., tightening and loosening). The control electronics may provide a control signal to the adjustment mechanism to control the adjustment of the gastric band.

The control electronics are also configured to control communications through the transceiver and/or to receive location information from the location detection electronics. More specifically, the control electronics may be configured to control the adjustment mechanism to controllably adjust the gastric band based, at least in part, on information received through the transceiver and/or information received from the location detection electronics.

Further embodiments may be configured to operate with other types of adjustable and/or inflatable devices, at least in part, based upon the geographic location of the devices, including, but not limited to an artificial sphincter, a device configured to be arranged for treatment or control of fecal incontinence, urinary incontinence, heartburn and/or acid reflux, or impotence, a facial implant device, a breast implant device, a penile implant device or other implantable cosmetic device. Yet further embodiments may be configured to operate and control a hearing aid.

BRIEF DESCRIPTION OF DRAWINGS

A brief description of preferred embodiments of the invention will be made with reference to the accompanying drawings, wherein.

DETAILED DESCRIPTION

The following detailed description is of the best presently contemplated mode of carrying out the invention. This description is not to be taken in a limiting sense, but is made merely for the purpose of illustrating the general principles of the invention. The scope of the invention is best defined by the appended claims.

Figure 1:
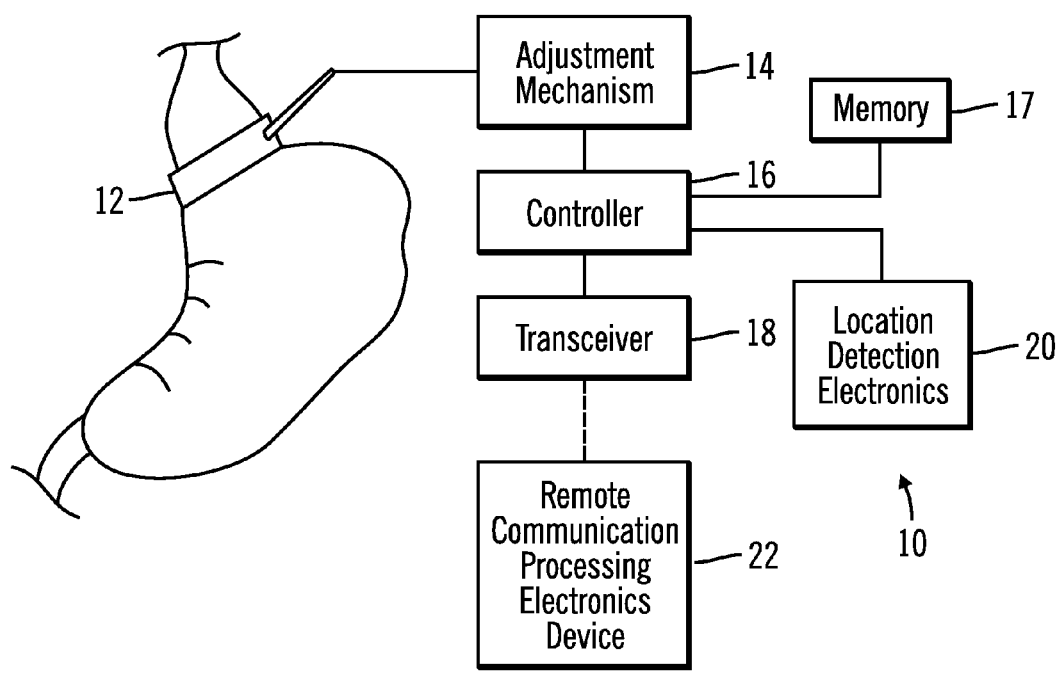
FIG. 1 is a generalized block diagram of a system according to an embodiment of the present invention.

FIG. 1 is a generalized block diagram, showing an example of a system 10 for controlling a gastric band based, at least in part, on geographic location. The system includes, but is not limited to, a gastric band 12 and adjustment mechanism 14 that controls the size of the stoma, control electronics 16 connected to control the adjustment mechanism 14 and electronic memory 17 associated with the control electronics. In addition, embodiments of the system 10 also include one or both of transceiver electronics 18 connected to the control electronics 16 and location detection electronics 20 connected to the control electronics. The transceiver electronics 18 may be configured for communication with a remote communication and processing device 22. The location detection electronics 20 provides a location signal corresponding to the geographic location of the system 10.

While not shown in FIG. 1, the system 10 includes a suitable power source for providing operational power to each of the components of the system 10. In one embodiment, each system component (including, but not limited to, the band 12, inflation source 14, processor 16, memory 17, transceiver 18 and location detection electronics 20) share a common power source. In other embodiments, one or more (or all) of the system components has its own power source that is not shared by other system components. In yet other embodiments, various system components may be connected in two or more groups to two or more respective power sources.

The gastric band 12 may be any suitable adjustable gastric band device, for example, but not limited to, an adjustable gastric band having a configuration as described in any one or combination of the following patents, but modified or connected to operate in accordance with the present disclosure: U.S. Pat. Nos. 7,351,240; 6,102,922; 5,449,368; 5,226,429; and 4,592,339, the entire contents of each of which is incorporated herein by reference. The gastric band 12 is configured to be implanted in a patient and fitted around a portion of a patient's stomach, to form a stoma between an upper portion and a lower portion of the patient's stomach. The gastric band 12 can reduce or slow down the passage of food to give the patient a sensation of reduced hunger or being full. The gastric band 12 is adjustable to adjust the size of the stoma and, thus, the sensation to the patient.

The adjustment mechanism 14 may be any suitable device for providing an adjustment force, pressure, signal or the like to the gastric band 12, to cause adjustment of the gastric band 12. The gastric band 12 may be adjustable in a first direction (for example, in a narrowing or tightening direction for reducing the volume or cross-sectional area of a portion of the stomach) and in a second direction opposite to the first direction (for example, in a broadening, loosening direction for increasing the volume or cross-sectional area of a portion of the stomach). In one example embodiment, the adjustment mechanism 14 may be a fluid conveying device for conveying (infusing) a fluid into the gastric band 12. An example of a suitable fluid infusing device is described in the above-referenced U.S. Pat. No. 7,351,240 (with reference to fluid infuser 40 described and illustrated in that patent). However, other embodiments may employ other suitable fluid infusing devices.

The control electronics 16 may include one or more suitable electronic processors or processing electronics configured (by hardware, firmware, software or combinations thereof, or the like) to operate in the manner described herein. The control electronics 16 are configured to control the operation of the adjustment mechanism 14 in accordance with control plans of embodiments of the present invention. The control electronics 16 may be an implantable structure configured to be implanted within the patient's body, for example, attached to, adjacent to or in the proximity of the gastric band 12 (or in another location on the patient's body, remote from the gastric band) and operatively connected to the adjustment mechanism by any suitable communication connection, such as, but not limited to wire conductors, wireless RF or the like. Alternatively, the control electronics 16 may be an external device (for example, but not limited to, a device configured similar to the programmer 52 described in the above-referenced U.S. Pat. No. 7,351,240). Other embodiments may employ other suitable control electronics 16 that operate as described herein.

The control electronics 16 may include or be operatively connected to an associated electronic memory 17. While the electronic memory 17 in FIG. 1 is represented by a single box in the system diagram, embodiments of electronic memory 17 may include one or more memory devices in or operative connected to the control electronics 16. For example, in one embodiment, the electronic memory 17 may include one or more ROM devices and one or more RAM devices, where the one or more ROM devices operate to store operation software, instructions and data for programming the control electronics to operate in a manner as described herein. The one or more RAM devices may operate to store further data used by the control electronics 16 during operation of the system 10. In further embodiments, the electronic memory may also include one or more ROM devices or other suitable static memory devices that retain stored information in the event of a loss of power, for storing operation software, data or other information, in the event of a system power failure, for retrieval and use after suitable power is restored.

The electronic memory 17 may be included in the control electronics 16. For example, by being provided on the same circuit board or arranged in the same housing structure as the rest of the control electronics 16.

In other embodiments, the electronic memory 17 may be external to the control electronics 16, but operatively connected to the control electronics. For example, the electronic memory 17 may be arranged in a separate housing structure that is mounted on or configured to be implanted adjacent to the band 12 and/or the processor 16. In other embodiments, at least some of the electronic memory 17 that is operatively coupled to the processor 16 may be located remote from the processor 16, for example, but not limited to, in or located with a remote communication and processing device 22.

The location detection electronics 20 may include, but are not limited to a satellite positioning device, such as a Global Positioning System (GPS) device, for providing a position signal representing the geographic location of the device (including a receiver associated with the device). In other embodiments, the location detection electronics 20 may include other suitable devices for providing a position signal representing geographic location, including, but not limited to devices that receive signals from one or more remote signal sources and use triangulation or other suitable position determining processes to provide a position signal representing a geographic location of the device and, thus, of the system 10.

In one embodiment, the location detection electronics 20 may be an implantable structure configured to be implanted within the patient's body, for example, attached to, adjacent to or in the proximity of the gastric band 12 (or in another location on the patient's body, remote from the gastric band) and operatively connected to the adjustment mechanism by any suitable communication connection, such as, but not limited to wire conductors, wireless RF or the like. Alternatively, the location detection electronics 20 may be an external device connected to the control electronics by any suitable communication connection, such as, but not limited to wire conductors, wireless RF or the like.

The transceiver electronics 18 may be any suitable communication electronics configured for communication with a remote communication and processing device 22. The transceiver 18 may be configured for wireless communication with a processing device 22, for example, but not limited to, communication via link that is wireless RF or other frequency, Bluetooth, optical, electromagnetic, inductive or the like. In one embodiment, the transceiver electronics 18 may be an implantable structure configured to be implanted within the patient's body, for example, attached to, adjacent to or in the proximity of the gastric band 12 (or in another location on the patient's body, remote from the gastric band) and operatively connected to the adjustment mechanism by any suitable communication connection, such as, but not limited to wire conductors, wireless RF or the like. Alternatively, the location transceiver electronics 18 may be an external device connected to the control electronics by any suitable communication connection, such as, but not limited to wire conductors, wireless RF or the like.

In one embodiment, the components of the system 10 may be contained in a single, common implantable housing structure configured to be implanted within the patient's body, for example, attached to the gastric band 12, to be implanted as a unit with the gastric band 12. In other embodiments, the system 10 may be contained in one or more implantable housing structures configured to be implanted in the patient's body, adjacent to or in the proximity of the gastric band 12 (or in another location on the patient's body, remote from the gastric band) and operatively connected to the adjustment mechanism by any suitable communication connection, such as, but not limited to wire conductors, wireless RF or the like. In other embodiments, some or all of the components of system 10 (other than the gastric band 12) may be configured to be external to the patient's body and coupled for communication with other components of the system 10 by any suitable communication connection, such as, but not limited to wire conductors, wireless RF or the like. Each implantable component of the system 10 may include its own respective power source (not shown), such as, but not limited to a battery or, alternatively, may be configured to share a common power source with one or more (or all) of the other components of the system 10.

The control electronics 16 are configured to control the operation of the adjustment mechanism 14 to controllably adjust the gastric band 12, for example, in either or both of the adjustment directions discussed above. The control electronics 16 may provide a first control signal to the adjustment mechanism 14 to control the adjustment of the gastric band 12.

The control electronics 16 are also configured to control communications through the transceiver 18 and/or to receive location information from the location detection electronics 20. More specifically, the control electronics 16 may be configured to control the adjustment mechanism 14 to controllably adjust the gastric band 12 based, at least in part, on information received through the transceiver 18 and/or information received from the location detection electronics 20.

The location detection electronics 20 may be configured to provide a signal representing the geographic location of the system 10 and, thus, the geographic location of the patient in which the gastric band 12 is implanted. In one embodiment, the signal provided by the location detection electronics 20 is a second control signal provided to the control electronics 16. In such an embodiment, the control electronics 16 may be configured to determine whether the geographic location represented by the second control signal is within a predefined region. That determination may be made, for example, but not limited to, comparing the geographic location represented by the second control signal with stored information representing one or more (such as a plurality of) predefined geographic regions. Such stored information may be stored, for example, in the electronic memory 17 and/or in external memory to which the system 10 may communicate, including, but not limited to, electronic memory associated with the remote communication and processing device 22.

Figure 2:
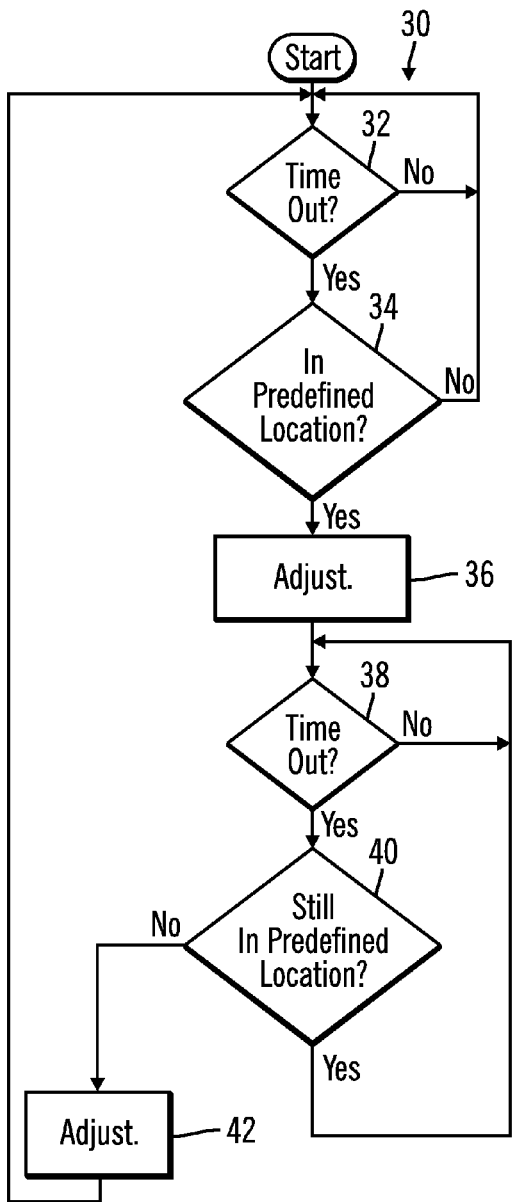
FIG. 2 is a generalized flow chart of a process and system operation according to an embodiment of the present invention.

In one example process 30, as represented by the flow chart of FIG. 2, the control electronics 16 determines 32 whether or not it is time to determine if the gastric band 12 is in a pre-defined region. That determination 32 may be made, for example, by referring to a timing signal from a timer or clock (not shown) included in the control electronics or otherwise operatively coupled to the control electronics 16. For example, a timer or clock may be configured to time a predefined time period (or consecutive predefined time periods) and provide a time-out signal upon reaching the predefined time period (or upon reaching each consecutive predefined time period). If the determination 32 is no (a time-out signal has not occurred), then the process returns to check again for a new time-out signal. The timer or clock may be restarted upon the return (or the process may simply return prior to or upon occurrence of the next consecutive time-out signal). If the determination 32 is yes (a time-out signal has occurred), then the process proceeds to a further determination 34. In other embodiments, the process may trigger to start at the determination 34 upon occurrence of a time-out signal in other suitable manners.

Upon a determination 32 of yes (a time-out signal has occurred), then the control electronics 16 makes a determination 34 regarding whether or not the band 12 is located in a predefined geographic location or region. If the determination 34 is no (the band 12 is determined to not be in a predefined geographic location or region), then the process returns to check again for a new time-out signal. The timer or clock may be restarted upon the return (or the process may simply return prior to or upon occurrence of the next consecutive time-out signal). If the determination 34 is yes (the band 12 is determined to be within a predefined geographic location or region), then the process proceeds to the adjustment 36.

The determination 34 may be made in any suitable manner including, but not limited to a procedure involving comparing the geographic location information (or position signal) provided by the location detection electronics 20 with pre-stored information corresponding to one or more predefined locations. The pre-stored information may be obtained from the electronic memory 17. In other embodiments, the determination 34 may be made by other suitable manners, including but not limited to comparing the geographic location information (or position signal) provided by the location detection electronics 20 with location information received in real time from an external source, for example, by communication through the transceiver 18, or using data corresponding to the geographic location information (or position signal) provided by the location detection electronics 20 in one or more mathematical formulas or algorithms that calculate a value (where the value is used for the determination 34, such as by defining a yes determination 34 if the value is above or below a pre-set threshold or at a pre-set value).

As noted above, if the determination 34 is yes (the band 12 is determined to be within a predefined geographic location or region), then the process proceeds to the adjustment 36. In particular, the controller 16 controls the adjustment mechanism 14 to adjust the band 12. The controller 16 may control the adjustment mechanism to adjust the band 12 in a manner consistent with a pre-defined adjustment amount. In one embodiment the pre-defined adjustment amount may be defined by a pre-stored adjustment scheme. For example, data representing one or more pre-stored adjustment schemes may be stored in the electronic memory 17 accessible by the controller 16. In one embodiment, each one of a plurality of pre-defined geographic locations or regions may be associated with a corresponding one of a plurality of pre-stored adjustment schemes, such that a different adjustment scheme is accessed and applied for each different pre-defined geographic location or region. In other embodiments, a plurality of groups of pre-defined geographic locations or regions may be associated with a corresponding one of a plurality of pre-stored adjustment schemes, such that a different adjustment scheme is accessed and applied for each different group of pre-defined geographic locations or regions (where each group of pre-defined geographic locations or regions comprises one or multiple pre-defined geographic locations or regions).

Upon completion of the adjustment 36 (or during adjustment 36), the control electronics 16 determines 38 whether or not it is time to determine if the gastric band 12 is in still in a pre-defined region. That determination 38 may be made, for example, by referring to a timing signal from a timer or clock (not shown) included in the control electronics or otherwise operatively coupled to the control electronics 16, as discussed above with respect to the determination 32. If the determination 38 is no (a time-out signal has not occurred), then the process returns to the determination 38 to check again for a new time-out signal. The timer or clock may be restarted upon the return (or the process may simply return prior to or upon occurrence of the next consecutive time-out signal). If the determination 38 is yes (a time-out signal has occurred), then the process proceeds to a further determination 40.

In particular, upon a determination 38 of yes (a time-out signal has occurred), then the control electronics 16 makes a determination 40 regarding whether or not the band 12 is still located in a predefined geographic location or region. If the determination 34 is yes (the band 12 is determined to still be in a predefined geographic location or region), then the process returns to the determination 38 to check again for a new time-out signal. The timer or clock may be restarted upon the return (or the process may simply return prior to or upon occurrence of the next consecutive time-out signal). If the determination 38 is no (the band 12 is determined to no longer be within a predefined geographic location or region), then the process proceeds to the adjustment 42. The determination 38 may be made in a manner similar to the manner discussed above with respect to the determination 34.

As noted above, if the determination 38 is no (the band 12 is determined to no longer be within a predefined geographic location or region), then the process proceeds to the adjustment 42. In particular, the adjustment 42 involves the controller 16 controlling the adjustment mechanism 14 to re-adjust the band 12. The controller 16 may control the re-adjustment mechanism to re-adjust the band 12 in a manner consistent with a pre-defined re-adjustment amount. In one embodiment, the pre-defined re-adjustment amount may be defined from pre-stored re-adjustment scheme for re-adjusting the band 12 after the band 12 exits a pre-defined geographic location or region. For example, data representing one or more pre-stored re-adjustment schemes may be stored in the electronic memory 17 accessible by the controller 16. In one embodiment, each one of a plurality of pre-defined geographic locations or regions may be associated with a corresponding one of a plurality of pre-stored re-adjustment schemes, such that a different re-adjustment scheme is accessed and applied for exiting each different pre-defined geographic location or region. In other embodiments, a plurality of groups of pre-defined geographic locations or regions may be associated with a corresponding one of a plurality of pre-stored re-adjustment schemes, such that a different re-adjustment scheme is accessed and applied exiting any one of the geographic locations or regions in each different group of pre-defined geographic locations or regions (where each group of pre-defined geographic locations or regions comprises one or multiple pre-defined geographic locations or regions).

Upon completion of the adjustment 42 (or during adjustment 42), the process may return to the determination 32. In this manner, the process may be continuous. In other embodiments, a mechanism and procedure (not shown) for exiting the process 30 or otherwise turning off the adjustment mechanism 14 or controller 16 may be provided to allow a manual (or automatic, in response to a pre-defined triggering event) termination of the process 30.

Figure 3:
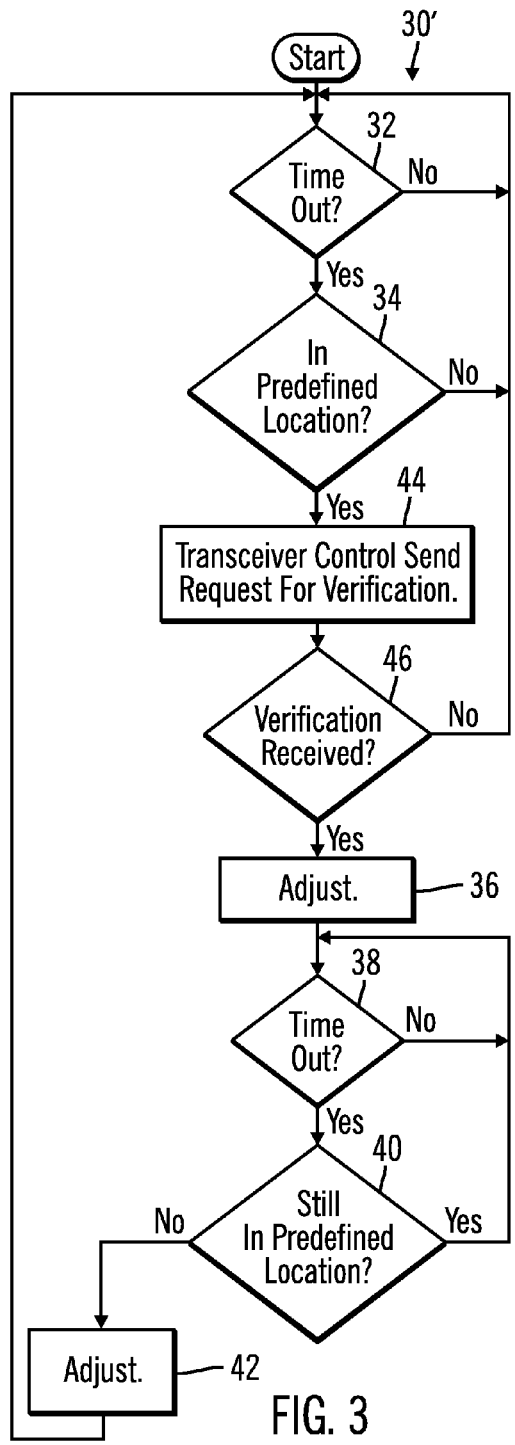
FIG. 3 is a generalized flow chart of a process and system operation according to a further embodiment of the present invention.

Another example process 30' is represented by the flow chart of FIG. 3. The process 30' corresponds to the process 30 discussed above with respect to FIG. 2, but with additional features between the determination 34 and the adjustment 36. In particular, corresponding features in process 30 and 30' are labeled with the same reference numbers and the above descriptions of those features are incorporated herein by reference. In process 30', upon a determination 34 of yes (the band 12 is determined to be within a predefined geographic location or region), then the process proceeds to the transceiver control 44, at which the controller 16 controls the transceiver to perform one or more communications.

In particular, the transceiver control 44 includes controlling the transceiver 18 to send a request for verification to the remote communication and processing device 22. Upon sending a request for verification 44, the process 30' proceeds to the determination 46 if a verification to adjust has been received. In particular, the transceiver 18 may be configured to receive a communication from a remote communication and processing device 22, in response to the request for verification. The communication received by the transceiver may comprise a verification to adjust or may include a denial of a verification (or the lack of a verification can function as a denial). In this manner, a medical practitioner, clinician, or other agent may be contacted upon the determination 34 that the band 12 is in a predefined geographic location or region, and prior to adjustment 36 of the band 12, to provide verification that the adjustment should be made. If the verification is not received (no at determination 46), then the process returns to check again for a new time-out signal. The timer or clock may be restarted upon the return (or the process may simply return prior to or upon occurrence of the next consecutive time-out signal). If the determination 46 is yes (verification to adjust was received), then the process proceeds to the adjustment 36 and continues to proceed thereafter as discussed above with respect to process 30. In further embodiments, a similar transceiver control for sending verification requests 44 and a determination of receipt of verification 46 may be provided after a no determination 40 and prior to an adjustment 42. Otherwise the process 30' may function similar to the process 30 discussed above.

Figure 4:
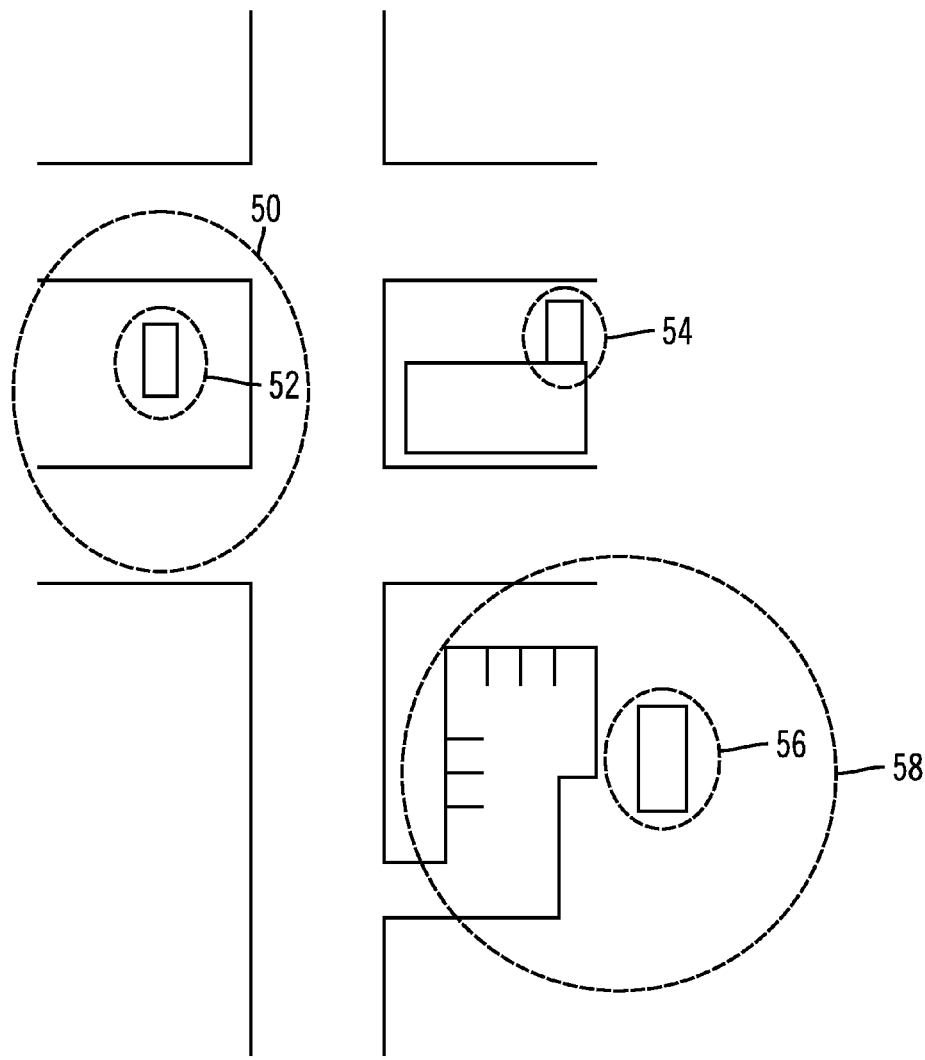
FIG. 4 is a generalized plan view of geographic regions associated with embodiments of the present invention.

Systems and processes as described above may be operated to control the band 12 in accordance with the geographic location of the band 12. For example, FIG. 4 shows a plan diagram or map that shows several predefined geographic regions 50, 52, 54, 58 and 60. In one embodiment, a predefined geographic region 52 may be fully within or surrounded by another predefined geographic region 50. Similarly, predefined geographic region 56 is fully within and surrounded by predefined geographic region 58. Other predefined geographic regions 54 may be discrete or separated from other pre-defined geographic region. In one embodiment, the controller 16 is controlled to provide a first level of adjustment upon a determination that the band 12 is in a first predefined geographic region 50 or 58, while a second level of adjustment may be provided upon a determination that the band 12 is in a second predefined geographic region 52 or 56 located within or surrounded by the first predefined geographic region 50 or 58. The first and second levels of adjustment may differ from each other.

For example, a first level of adjustment that is not as great as the second level of adjustment. In this manner, the first predefined geographic region 50 or 58 may correspond to a geographic region that is near to an eating establishment or other region or location at which the user of the band 12 may be enticed to consume inappropriate food. For example, the regions 50 and 58 may correspond to parking lots of predefined restaurants, fast food locations, grocery stores, or the like, while regions 52 and 56 correspond to the physical structures of such restaurants, food locations, grocery stores, or the like. In further example embodiments, the band may be configured to respond to further levels of adjustment, for different regions. In yet further examples of each of the above embodiments, the system may be configured to receive user input, to allow the user (therapist, medical practitioner or the like) to identify one or more predefined regions (such as region 54) and/or multiple levels of regions (such as regions 50, 52, 56 and 58). In one example, a region 54 may correspond to the geographic location of a user's home, or a portion of the user's home, such as, but not limited to, the kitchen, refrigerator, pantry or other source of food commonly accessible to the user. In other embodiments, the region 54 may correspond to other suitable geographic locations at which control of the band 12 is desired.

While various embodiments described above relate to systems and processes in which a band 12 is controlled to adjust in a first direction (for example, in a narrowing or tightening direction for reducing the volume or cross-sectional area of a portion of the stomach) upon a determination that the band 12 is located in a predefined geographic region, other embodiments may be configured to control the band 12 to adjust in a second direction (in a broadening or loosening direction) upon a determination that the band 12 is located in a pre-defined geographic region. For example, such embodiments may be configured to broaden or loosen the band, upon the band (and, thus, the user) being determined to be in a safe region, such as the user's home, a patient care facility, a predefined eating establishment, or the like.

Also, while the embodiment in FIG. 1 relates to systems and processes in which a band 12 is arranged around a portion of a user's stomach, other embodiments may be configured to operate with a band arranged around a different portion of a user's anatomy. For example, the band 12 may be an artificial sphincter, configured to be arranged for treatment or control of fecal incontinence, for example, as described in U.S. Pat. No. 6,461,292, which is hereby incorporated herein by reference, in its entirety. As another example, the band 12 may be configured to be arranged for treatment of urinary incontinence, for example, as described in U.S. Patent Application Publication No. 2003/0105385, which is hereby incorporated herein by reference, in its entirety. As yet another example, the band 12 may be configured to be arranged for treatment of heartburn and/or acid reflux, for example, as described in U.S. Pat. No. 6,470,892, which is hereby incorporated herein by reference, in its entirety. As yet another example, the band 12 may be configured to be arranged for treatment of impotence, for example, as described in U.S. Patent Application Publication No. 2003/0114729, which is hereby incorporated herein by reference, in its entirety. In each such other example embodiments, the band 12 may be controlled, at least in part, based upon the geographic location of the band 12, as described above.

In yet other embodiments, the band 12 may be configured to be implanted under a user's skin around a desired portion of a user's body (including limbs), including, but not limited to the mid-section of the torso or other suitable body part. In yet other embodiments, the band 12 (or other suitable inflatable member) may be configured to be arranged external to a user's skin, for example, but not limited to, in a belt, girdle, wrap or other structure configured to be arranged external to and around a desired portion of a user's body. In each such other example embodiments described above, the band 12 (or other suitable inflatable member) may be controlled, at least in part, based upon the geographic location of the band 12 (member), as described above.

In yet other embodiments, other types of implantable medical, therapeutic or cosmetic devices that employ one or more controllable hydraulically inflatable member (as described in U.S. Pat. No. 7,351,240, which has been incorporated herein by reference in its entirety) may be configured and operated in accordance with embodiments of the present invention to be controlled for inflation and/or deflation, at least in part, based upon the geographic location of the inflatable member, as described above. Such other devices may include, but are not limited to facial implants, breast implants, penile implants or other implantable cosmetic devices.

In each of the example embodiments described above, the band 12 or other inflatable member may be configured, for example, for medical, therapeutic and/or cosmetic purposes.

In further embodiments, the band 12 (or other inflatable member) may be configured to detect certain types of malfunctions of the band (member) or associated control electronics) and, in response to such detection, perform one or more predefined functions. The predefined functions may include providing an alarm or other suitable notification message to the user, for example, by providing an audible, tactile or visual signal to the user. Alternatively or in addition, the predefined functions may include contacting a physician, treatment facility or the like, for example, by electronic communication with a remote device 22 associated with the physician, facility, etc., through the transceiver 18. In one such embodiment, the physician, treatment facility or the like may be contacted based on the geographic location detected by the electronics 20, such that, for example, one or more of the closest available physicians, facilities, etc. with respect to the detected geographic location may be contacted. In such embodiments that employ external control electronics, the system may be configured to provide the user with information corresponding to the location, address, directions to the location, or the like, of one or more of the closest available physicians, facilities, etc. with respect to the detected geographic location, for example, on a user interface associated with the external control electronics.

In further embodiments, other features may be associated and included with the system 10. For example, in embodiments that employ external control electronics, the system 10 may be configured to provide the user with information associated with the detected location, including, but not limited to promotional material that may be of interest to the user based on the user's geographic location, or information (name, location, email address, text mail address, or the like) relating to other users of systems similar to system 10 within a specified distance from the detected geographic location of the system 10 (for example, to provide a peer-to-peer communication link to such other users), or the like. In further embodiments, the system 10 may include embedded secure identification electronics, for example, to provide automatic secure access rights. Such secure identification electronics may provide a signal (through the transceiver 18, another transmitter, or other signal producing devices) detectable by external devices that function, in response to the detection of the signal, to identify the user, unlock electronic locking devices, enable electronic devices, enable access, or the like.

The embodiments disclosed herein are to be considered in all respects as illustrative and not restrictive of the invention. The scope of the invention is indicated by the appended claims, rather than the foregoing description. All changes that come within the meaning and range of equivalency of the claims are therefore intended to be embraced therein.

What is claimed is:

1. A system for treating a patient, the system comprising:
a gastric band device configured to be adjustable in response to an adjustment control signal;
one or both of a receiver device and a location detection device, wherein one or both of the receiver device and the location detection device is configured for generating at least one control signal, which is based on a geographic location of the gastric band device, wherein the geographic location of the gastric band device is determined by one or both of the location detection device and an external communication device in communication with the receiver device; and
a controller in communication with the gastric band device and one or both of the receiver device and the location detection device, wherein the controller is configured to transmit the adjustment control signal to the gastric band device based at least in part on the at least one control signal.

2. The system of claim 1, wherein the location detection device is configured to determine a geographic location of the gastric band device and to generate the at least one control signal.

3. The system of claim 1, wherein the controller is configured to provide the adjustment control signal for increasing restriction or decreasing restriction of the gastric band device in response to receiving a control signal indicating that the gastric band device is located within a predefined geographic region.

4. The system of claim 3, wherein the adjustment control signal causes restriction of the gastric band device by a first amount in response to a first control signal indicating that the gastric band device is located within a first predefined geographic region, and wherein the adjustment control signal causes restriction of the gastric band device by a second amount in response to a second control signal indicating that the gastric band device is located within a second predefined geographic region.

5. The system of claim 3, further comprising:
a timing mechanism in communication with the controller and configured to deliver a timing signal to trigger the controller to determine whether the gastric band device is located within the predefined geographic region.

6. The system of claim 1, further comprising:
electronic memory in communication with the controller and configured to store data relating to one or more predefined geographic regions, wherein the controller is configured to transmit the adjustment control signal for either increasing restriction or decreasing restriction of the gastric band device in response to receiving a signal indicating whether the gastric band device is located within the one or more predefined geographic regions.

7. The system of claim 6, wherein the adjustment control signal increases restriction of the gastric band device by a first amount in response to a first control signal indicating that the gastric band device is located within a first predefined geographic region, and wherein the adjustment control signal increases restriction of the gastric band device by a second amount in response to a second control signal indicating that the gastric band device is located within a second predefined geographic region.

8. The system of claim 6, wherein the one or more predefined geographic regions stored in the electronic memory include a restaurant, a grocery store, or an eating establishment, and wherein the controller is configured to transmit the adjustment control signal for increasing restriction of the gastric band device in response to receiving a signal from the location detection device indicating that the gastric band device is located within the one or more predefined geographic regions.

9. The system of claim 6, further comprising:
an input device in communication with the electronic memory, the input device configured to receive input from a health professional defining the one or more predefined geographic regions and defining an adjustment amount in the adjustment control signal for each of the one or more predefined geographic regions.

10. The system of claim 1, wherein the receiver is configured to receive an external communication signal from the external communication device and provide the at least one control signal in response to receiving the external communication signal.

11. The system of claim 10, further comprising:
a transmitter in communication with the controller and configured to transmit an indicator signal to the external communication device in response to the at least one control signal.

12. A method for controlling a gastric band device, the method comprising:
generating at least one first control signal indicating a geographic location of the gastric band device;
generating at least one second control signal based in part on the at least one first control signal; and
adjusting the gastric band device in response to the at least one second control signal, thereby adjusting the gastric band device based on the geographic location of the gastric band device.

13. The method of claim 12, wherein the at least one first control signal comprises a signal that indicates the geographic location of the gastric band device, and the method further comprises:
generating the signal that indicates the geographic location of the gastric band device.

14. The method of claim 13, further comprising:
increasing restriction or decreasing restriction of the gastric band device in response to a first control signal indicating that the gastric band device is located within a predefined geographic region.

15. The method of claim 14, further comprising:
determining whether the gastric band device is located within the predefined geographic region based on a timing signal.

16. The method of claim 12, further comprising:
increasing restriction or decreasing restriction of the gastric band device in response to receiving a first control signal indicating that the gastric band device is located within a predefined geographic region.

17. The method of claim 16, further comprising:
causing restriction of the gastric band device by a first amount in response to a first signal indicating that the gastric band device is located within a first predefined geographic region; and
causing restriction of the gastric band device by a second amount in response to a second signal indicating that the gastric band device is located within a second predefined geographic region.

18. The method of claim 12, further comprising:
storing data that relates to one or more predefined geographic regions; and
transmitting the at least one second control signal for either increasing restriction or decreasing restriction of the gastric band device in response to receiving a first control signal indicating whether the gastric band device is located within the one or more predefined geographic regions.

19. The method of claim 18, further comprising:
causing restriction of the gastric band device by a first amount in response to a first signal indicating that the gastric band device is located within a first predefined geographic region; and
causing restriction of the gastric band device by a second amount in response to a second signal indicating that the gastric band device is located within a second predefined geographic region.

20. The method of claim 18, wherein the one or more predefined geographic regions include a restaurant, a grocery store, and an eating establishment, and wherein the method further comprises:
transmitting the adjustment control signal for increasing restriction of the gastric band device in response to receiving a signal indicating that the gastric band device is located within the one or more predefined geographic regions.

21. The method of claim 18, further comprising:
receiving input from a health professional defining the one or more predefined geographic regions and defining an adjustment amount for each of the one or more predefined geographic regions.

22. The method of claim 12, further comprising:
receiving, via an external communication device, an external communication signal; and
generating the at least one first control signal in response to receiving the external communication signal.

23. The method of claim 22, further comprising:
transmitting an indicator signal to the external communication device in response to the at least one first control signal.

24. A system for treating a patient, the system comprising:
an adjustable member attachable to bodily tissue and operable to adjustably apply mechanical pressure to the bodily tissue, the adjustable member in communication with an adjustment mechanism configured to adjust the adjustable member;
one or both of a receiver device and a location detection device, the receiver device configured for receiving a first control signal based on a geographic location of the adjustable member and the location detection device configured for generating a second control signal indicating a geographic location of the adjustable member; and
a controller in communication with the adjustment mechanism and one or both of the receiver device and the location detection device, the controller configured to receive one or both of the first and second control signals and to generate an adjustment control signal based on one or both of the first and second control signals, the controller further configured to transmit the adjustment control signal to the adjustment mechanism for adjusting the adjustable member based on the adjustment control signal.

25. The system of claim 24, wherein the location detection device is configured to determine a geographic location of the adjustable member and to generate the second control signal indicating the geographic location of the adjustable member.

26. The system of claim 25, wherein the controller is configured to provide an adjustment control signal to the adjustment mechanism for adjusting the adjustable member in response to the controller receiving a signal from the location detection device indicating that the adjustable member is located within a predefined geographic region.

27. The system of claim 26, wherein the adjustable member is a gastric band device, and wherein the adjustment control signal causes the adjustment mechanism to restrict the gastric band device by a first amount in response to the location detection device generating the second control signal indicating that the gastric band device is located within a first predefined geographic region, and wherein the adjustment control signal causes the adjustment mechanism to restrict the gastric band device by a second amount in response to the location detection device generating the second control signal indicating that the gastric band device is located within a second predefined geographic region.

28. The system of claim 27, further comprising:
electronic memory in communication with the controller and configured to store data relating to one or more predefined geographic regions, wherein the controller is further configured to determine whether the adjustable member is located within the one or more predefined geographic regions based on the second control signal from the location detection device and wherein the adjustment control signal is based on whether the adjustable member is located within the one or more predefined geographic regions.

29. The system of claim 24, wherein the receiver device is configured to receive an external communication signal from an external communication device and generate the first control signal in response to receiving the external communication signal.

30. The system of claim 29, further comprising:
a transmitter in communication with the controller and configured to transmit an indicator signal to the external communication device in response to the second control signal generated by the location detection device.

31. The system of claim 24, wherein the adjustable member includes one of an artificial sphincter, urinary bladder device, facial implant, breast implant, and penile implant.

* * * * *